(12) United States Patent
Taniguchi et al.

(10) Patent No.: US 9,101,558 B2
(45) Date of Patent: Aug. 11, 2015

(54) USE OF ANTI-CANCER CELL COMPOSITION FOR TREATMENT OF HEAD AND NECK CANCER, WHICH IS INTENDED TO BE ADMINISTERED TO NUTRIENT ARTERY OF TUMOR

(75) Inventors: Masaru Taniguchi, Yokohama (JP); Shigetoshi Horiguchi, Chiba (JP); Yoshitaka Okamoto, Chiba (JP); Toshinori Nakayama, Chiba (JP)

(73) Assignee: National University Corporation Chiba University, Chiba (JP)

( * ) Notice: Subject to any disclaimer, the term of this patent is extended or adjusted under 35 U.S.C. 154(b) by 1231 days.

(21) Appl. No.: 12/679,923

(22) PCT Filed: Sep. 26, 2008

(86) PCT No.: PCT/JP2008/067416
§ 371 (c)(1),
(2), (4) Date: Feb. 10, 2011

(87) PCT Pub. No.: WO2009/041573
PCT Pub. Date: Apr. 2, 2009

(65) Prior Publication Data
US 2011/0142813 A1    Jun. 16, 2011

(30) Foreign Application Priority Data
Sep. 26, 2007  (JP) .................................. 2007-250023

(51) Int. Cl.
*A61K 39/00* (2006.01)
*C12N 5/0783* (2010.01)
*C12N 5/0784* (2010.01)

(52) U.S. Cl.
CPC .......... *A61K 39/0011* (2013.01); *C12N 5/0639* (2013.01); *C12N 5/0646* (2013.01); *A61K 2039/5154* (2013.01); *A61K 2039/5158* (2013.01); *A61K 2039/544* (2013.01); *C12N 2501/2302* (2013.01)

(58) Field of Classification Search
None
See application file for complete search history.

(56) References Cited

U.S. PATENT DOCUMENTS

2010/0129339 A1    5/2010  Taniguchi et al.

OTHER PUBLICATIONS

Uchida et al. (Cancer Immunology, Immunotherapy, vol. 57, No. 3, pp. 337-345; electronically available Aug. 10, 2007); of record.*
(Continued)

*Primary Examiner* — Cherie M Stanfield
*Assistant Examiner* — Paul D. Pyla
(74) *Attorney, Agent, or Firm* — Kilyk & Bowersox, P.L.L.C.

(57) ABSTRACT

To provide a method of efficiently delivering cells having an anti-tumor activity to tumor tissues to evoke a stronger anti-tumor reaction, and a method of providing a more effective tumor regression effect, both in a cellular immunotherapy for cancer utilizing cells having an anti-tumor activity or antigen presenting cells for activating cells capable of exhibiting an anti-tumor activity. Provided are: a method of treating head and neck cancer, comprising administering an anti-cancer cell composition containing NKT cells activated in vitro with an NKT cell ligand into the tumor-feeding artery, and administering an NKT cell-stimulating agent containing antigen presenting cells treated with an NKT cell ligand through the upper respiratory tract mucous membrane; a use, in anti-cancer treatment of head and neck region, of the anti-cancer cell composition and the NKT cell-stimulating agent; a kit comprising the anti-cancer cell composition and the NKT cell-stimulating agent; and the anti-cancer cell composition.

9 Claims, 3 Drawing Sheets (56) References Cited

OTHER PUBLICATIONS

Nieda et al.("Therapeutic activation of Va24+Vp11+ NKT cells in human subjects results in highly coordinated secondary activation of acquired and innate immunity," Blood, vol. 103, pp. 383-389; 2003); of record.*

Nakayama et al. (Abstract Book of the 11th Annual Meeting of the Society for Fundamental Cancer Immunology, May 25, 2007, p. 25 (of record).*

Nakayama, T., Abstract of the 3rd Cancer Progress Report Meeting of Cancer TR Project of the Ministry of Education, Culture, Sports, Science, and Technology of Japan, Mar. 3, 2007 (of record).*

Kunii et al. (Abstract Book of the 11th Annual Meeting of the Society for Fundamental Cancer Immunology, May 25, 2007, p. 75 (of record).*

Nakayama, "Research for developing an immune-cell therapy for head and neck cancer that targeted on the NKT cell immune system," Abstract of the 3rd Cancer Progress Report Meeting of Cancer TR Project of the Ministry of Education, Culture, Sports, Science, and Technology of Japan, Mar. 3, 2007 (in Japanese with English translation attached) (15 pages).

Okamoto et al., "Introduction of cellular immunotherapy and heavy particle radiotherapy for pharyngeal cancer," Chiba University, COE Report, 2005, p. 116-130 (in Japanese with English translation attached) (46 pages).

Kunii et al., "Phase I/II Study of Activated NKT Cells and αGalCer-pulsed Dendritic Cells in Patients with Locally Recurrent Head and Neck Cancer," Abstract Book of the 11th Annual Meeting of the Society for Fundamental Cancer Immunology, May 25, 2007, p. 75 (in Japanese with English translation attached) (3 pages).

Nakayama et al., "Combination therapy of activated NKT Cells and αGalCer-pulsed APCs in Patients with Locally Recurrent Head and Neck Cancer," Abstract Book of the 11th Annual Meeting of the Society for Fundamental Cancer Immunology, May 25, 2007, p. 25 (in Japanese with English translation attached) (3 pages).

Uchida et al., "Trials of NKT cell therapy in malignant tumor of Nasal cavity," The Oto-Rhino-Laryngological Society of Japan, May 20, 2005, vol. 108, No. 5, p. 606 (in Japanese with English translation attached) (4 pages).

* cited by examiner

USE OF ANTI-CANCER CELL COMPOSITION FOR TREATMENT OF HEAD AND NECK CANCER, WHICH IS INTENDED TO BE ADMINISTERED TO NUTRIENT ARTERY OF TUMOR

TECHNICAL FIELD

This application is a National Stage Application of PCT/JP2008/067416, filed Sep. 26, 2008, which claims the priority of Japanese Patent Application No. 2007-250023, which are incorporated herein by reference.

The present invention relates to: a method of treating head and neck cancer, comprising administrating an anti-cancer cell composition into the tumor nutrient artery and administering an NKT cell stimulating agent through the upper respiratory tract mucous membrane; a use, in treatment of head and neck cancer, of an anti-cancer cell composition to be administered into the tumor-feeding artery and an NKT cell stimulating agent to be administered through the upper respiratory tract mucous membrane; a kit comprising the anti-cancer cell composition and the NKT cell stimulating agent; and the anti-cancer cell composition. To be more specific, the present invention relates to: a method of treating head and neck cancer, comprising administrating an anti-cancer cell composition that contains NKT cells activated in vitro with an NKT cell ligand into the tumor-feeding artery, and administering an NKT cell stimulating agent that contains antigen presenting cells treated with an NKT cell ligand through the upper respiratory tract mucous membrane; a use, in treatment of head and neck cancer, of the anti-cancer cell composition to be administered into the tumor-feeding artery and the NKT cell stimulating agent to be administered through the upper respiratory tract mucous membrane; a kit comprising the anti-cancer cell composition to be administered into the tumor-feeding artery and the NKT cell stimulating agent to be administered through the upper respiratory tract mucous membrane; and the anti-cancer cell composition to be administered into the tumor-feeding artery.

BACKGROUND ART

For advanced cases in stage III and stage IV of head and neck squamous cell carcinomas, triple combination therapy comprising surgery, radiation, and chemotherapy is performed as a rule. With respect to surgical treatment, autologous tissue transplantation of free flaps, intestine, and bone with vascular stalk became popular particularly after the last half of the 1980s, which made extended resection relatively easy procedure and also provided specific effects on maintenance of functions and morphology, resulting in remarkable improvement of local control (Non-patent Document 1). Even absolute resection of cancers infiltrating the internal carotid artery or skull base became possible (Non-patent Document 2 and Non-patent Document 3). However, in the case of the extended range of resection, functional and morphological retention by reconstructive surgery are limited, and remarkable deterioration of the QOL of patients is caused. Further, in stage IV, a combination of radiation and chemotherapy is indispensable to improve therapeutic outcomes; however, in stage IV, for N2c and N3 cases and cases of infiltration in the carotid artery, therapeutic outcomes were poor even with extended resection, and the 5-year survival rate was lower than 50% (Non-patent Document 4). In a treatment comprising extended resection followed by a combination of radiation and chemotherapy, the survival rate improved significantly, but functional preservation for the larynx and the like was difficult.

Meanwhile, in Japan, since the launch of a platinum preparation in 1985, the preparation has been used as a neo-adjuvant or adjuvant therapy with the expectation for high efficacy of chemotherapy (Non-patent Document 5 and Non-patent Document 6). However, randomized studies in Europe and the US have almost resulted in conclusion by about 10 years previously that neo-adjuvant treatment does not contribute to the improvement in survival rate, compared with radiation monotherapy, though it is somewhat effective for functional preservation (Non-patent Document 7). At present, concurrent combination therapy comprising radiation therapy and chemotherapy is attracting attention as the central treatment for triple combination therapy, and randomized studies have reported that this therapy is more likely to achieve functional retention than radiation monotherapy, and also contributes to an improvement in survival rate (Non-patent Document 8). However, the improvement in survival rate is up to 0 to 8% and the 5 years survival rate is about 20 to 40%; moreover, many studies have excluded N2c, N3, or advanced T4 cases from the study populations. Additionally, the results of salvage surgery are poor (Non-patent Document 9).

Thus, the treatment of advanced head and neck squamous cell carcinomas, whether by surgery, radiation, or chemotherapy, poses major problems. To improve the results, and to lessen the burden on patients, a new therapeutic strategy is indispensable (Non-patent Document 10).

Natural killer T cells (NKT cells) are unique cells expressing both a T cell receptor (TCR) and a natural killer cell receptor (NKR) on the same cell surface, and were first reported as the fourth lymphocytes distinct from T cells, B cells, and natural killer cells (NK cells) (Non-patent Document 11, Non-patent Document 12, and Non-patent Document 13). The TCR on NKT cells is composed of an extremely limited α chain (Vα14-Jα281 in mice and Vα24-JαQ in humans) and β chain (Vβ8, Vβ7, or Vβ2 in mice and Vβ11 in humans) (Non-patent Document 14, Non-patent Document 15, Non-patent Document 16, Non-patent Document 17, and Non-patent Document 18), and it has been revealed that a molecule recognized thereby is a CD1d molecule, which is an antigen presenting molecule similar to major histocompatibility complex (MHC) Class I (Non-patent Document 19 and Non-patent Document 20). Recently, it was shown that the presentation of α-galactosylceramide, one of glycolipids, on CD1d could specifically activate NKT cells (Non-patent Document 21 and Non-patent Document 22). NKT cells activated with a ligand produce a large amount of interferon γ (IFN-γ) and interleukin-4 (IL-4) and exhibit potent cytotoxic activity via perforin/granzyme B. NKT cells activated with a ligand were thereafter clarified to have a unique action mechanism where various immune reactions are induced, and as a result, a strong anti-tumor action is exhibited. It has been reported that in various liver metastasis models of mice, α-galactosylceramide exhibited a remarkable anti-tumor effect that depends on NKT cells (Non-patent Document 23, Non-patent Document 24, and Non-patent Document 25). It was also found that α-galactosylceramide can specifically activate not only mouse NKT cells but also human NKT cells (Non-patent Document 26). Based on these results, a phase I clinical study with administration of α-galactosylceramide directed to patients with solid cancers has been performed in the Netherlands (Non-patent Document 27). Further, a lung cancer therapy involving infusion of NKT cells activated with α-galactosylceramide has been conducted, but no clear effect on tumor regression has been observed (Non-patent Document 28).

Dendritic cells (DCs) are the most potent antigen presenting cells in a T cell-dependent immune response. In cancer patients, it is said that DCs are inhibited in their maturation, activation, and mobilization by interleukin-10 (IL-10), vascular endothelial growth factor (VEGF) and the like that are secreted from tumors. Meanwhile, DCs are expected to overcome the above-mentioned condition where in vivo maturation and activation of DCs are suppressed and to serve an effective treatment, when taking out DC precursors from the body, leading them to a maturation process, further pulsing them with a tumor-specific antigen to impart a tumor antigen-specific immuno-reactivity, and then retransfusing the cells into the cancer patient. Clinical studies of a cancer vaccine therapy with DCs (DC therapy) have already started for malignant lymphoma, malignant melanoma, multiple myeloma, prostate cancer, renal cell carcinoma, and the like, and it has been preliminary reported that induction of antigen-specific cytotoxic T cells (CTLs) and tumor regression effects were observed. Reported adverse effects associated with the DC therapy include chill, fever, and the like. Development of autoantibodies (anti-thyroid antibody and the like) and having onset of chronic rheumatoid arthritis have been reported worldwide as adverse effects, but other severe adverse effects and complications have not been reported. Thus, the DC therapy is thought to be a relatively safe treatment method. However, general DC therapies utilizing tumor-specific molecules have such problems that their effect is expected only on the limited kind of tumors because of the specificity, and that tumor cells inpatients having different MHC or having reduced expression of MHC class I could not be targeted by CTL, because of MHC restriction.

Meanwhile, the above-mentioned anti-tumor action mechanism of α-galactosylceramide led to such an expectation that an anti-tumor effect should be obtained by transferring α-galactosylceramide-pulsed DCs into cancer-bearing mice. The results of examinations using animals showed that delayed timing of α-galactosylceramide administration in a malignant tumor metastasis model resulted in disappearance of the metastasis suppressing effect, whereas administration of α-galactosylceramide-pulsed DCs to cancer-bearing mice resulted in almost complete suppression of a lung or liver metastasis even when the timing of administration was delayed to some extent (Non-patent Document 29). This suggests that the administration of α-galactosylceramide in the form of being presented on DCs is more preferable than the administration of α-galactosylceramide itself in order to achieve efficient activation of NKT cells in vivo. Besides, since a CD1d molecule-NKT cell antigen receptor system utilized in this treatment method is common in all humans, NKT cells of anyone may be activated with α-galactosylceramide. Further, since activated NKT cells exhibit cytotoxic activity regardless of the expression of a MHC class I molecule, it is conceivable that the treatment method should have an advantage of complementing drawbacks of such a DC therapy as pulsing a cancer-specific peptide.

The safety trial of "treatment method using α-galactosylceramide (KRN 7000)-pulsed cells directed to lung cancer recurrent cases and patients with advanced lung cancer" approved by Ethics Committee of Chiba University revealed that an α-galactosylceramide-pulsed dendritic cell therapy may be performed safely. Further, the safety test of "clinical study using activated NKT cells directed to lung cancer recurrent cases and cases with advanced lung cancer" revealed that the intravenous administration of the activated NKT cells may be performed safely.

The intravenous administration of α-galactosylceramide-pulsed dendritic cells has been hitherto examined mainly for recurrent cases of lung cancer. The phase I study was conducted with escalation of the number of transferring cells from $5 \times 10^7/m^2$ at level 1 to $2.5 \times 10^8/m^2$ at level 2 and $1 \times 10^9/m^2$ at level 3. As a result, an increase in peripheral blood NKT cells was observed in one case out of total 11 cases participated in this study, where the cells at the number of level 3 was administered (Non-patent Document 30). However, α-galactosylceramide-pulsed dendritic cells at the number of level 1 and level 2 did not provided such an immune response where NKT cells increase in peripheral blood.

As described above, the administration of antigen presenting cells pulsed with an NKT cell ligand such as α-galactosylceramide can more efficiently stimulate NKT cells, stimulate an immunity, and treat diseases such as tumors, as compared to the in vivo direct administration of the NKT cell ligand.

The inventors of the present invention have reported that when dendritic cells pulsed with an antigen were administered through the nasal mucosa, the dendritic cells migrated the cervical lymph node highly selectively. The inventors have also confirmed that NKT cells were not detected in the normal non-metastatic cervical lymph node, while numerous NKT cells were detected in the cervical lymph node with metastasized head and neck cancer (Non-patent Document 31 and Non-patent Document 32).

Further, the inventors of the present invention have found that the administration of NKT cell ligand-pulsed antigen presenting cells through the upper respiratory tract mucous membrane induces NKT cells selectively in the cervical lymph node while NKT cells are usually not present in the cervical lymph node. The inventors have also found that the use of the administration method allows efficient stimulation of NKT cells with very small amount of antigen presenting cells also in tissues (such as peripheral blood) other than the cervical lymph node, and stimulation of a systemic immune response (Patent Document 1).

As described above, a cellular immunotherapy of cancer has been developed by utilizing, for example, cells having an anti-tumor activity or antigen presenting cells for activating cells capable of exhibiting an anti-tumor activity.

Meanwhile, in treatment of cancer, the selective intraarterial infusion of an anti-cancer drug has been widely used in a standard treatment. The selective intraarterial infusion therapy is a treatment method involving administering an anti-cancer drug directly into the tumor nutrient blood vessel, and thereby allowing a high concentration of a medicament to be distributed to a tumor, to enhance an anti-tumor effect and enhance a therapeutic effect, and to reduce a medicament circulating throughout the body to alleviate adverse effects. Also in head and neck cancer, a selective intraarterial infusion therapy of an anti-cancer drug has been developed, and there is a report that this therapy showed low improvement rate of the survival rate in the case of using the therapy alone, but improved a survival rate as well as a local control rate in a combination therapy with radiotherapy (Non-patent Document 33).

However, it has not been known whether the intraarterial administration of activated cells having an anti-tumor activity to the tumor nutrient blood vessel can efficiently deliver those cells to tumor tissues, and whether the administration can provoke a stronger anti-tumor reaction.

Patent Document 1: WO 2007/043630
Non-patent Document 1: Okamoto Yoshitaka, "Treatment of Advanced Head and Neck Cancer—Management and Problems", Jibi-Rinsho 2001 94:577-85

Non-patent Document 2: Okamoto Yoshitaka, "Challenge for cancer infiltrating the internal carotid artery", Jibiten 1999 42:232-9

Non-patent Document 3: Chazono H et al., "Extra-intracranial bypass for reconstruction of internal carotid artery in the management of head and neck cancer", Ann Vasc Surg 2003 17:260-5

Non-patent Document 4: Okamoto Y et al., "Carotid artery resection for head and neck cancer", Surgery 1996 120:54-9

Non-patent Document 5: Okamoto Y et al., "Arterial chemoembolization with cisplatin microcapsules", Br J Cancer 1986 53:369-75

Non-patent Document 6: Tomura N et al., "Chemoembolization of head and neck cancer with carboplatin-microcapsules", Acta Radiologica 1996 37:52-6

Non-patent Document 7: Rischin D, "Head and neck cancer debate: Does induction chemotherapy remain a worthy approach?", Am Soc Clin Oncol 2003 :300-4

Non-patent Document 8: Adelstein D J et al., "Mature results of a phase III randomized trial comparing concurrent chemotherapy with radiation alone in patients with stage III and IV squamous cell carcinoma of the head and neck", cancer 2000 88:876-83

Non-patent Document 9: Forastiere A A et al., "Concurrent Chemotherapy and radiotherapy for organ preservation in advanced laryngeal cancer", N Engl J Med 2003 349:2091-8

Non-patent Document 10: Okamoto Yoshitaka, "Treatment of Head and Neck Cancer: Problems and management", Chiba-Igaku 2003 79:1-5

Non-patent Document 11: Fowlkes B J et al., "A novel population of T-cell receptor alphabeta-bearing thymocytes which predominantly expresses a single V beta gene family", Nature 1987 Sep. 17-23; 329(6136):251-4

Non-patent Document 12: Budd R C et al., "Developmentally regulated expression of T cell receptor beta chain variable domains in immature thymocytes", J Exp Med 1987 Aug. 1; 166(2):577-82

Non-patent Document 13: Imai K et al., "Sequence and expression of transcripts of the T-cell antigen receptor alpha-chain gene in a functional, antigen-specific suppressor-T-cell hybridoma", Proc Natl Acad Sci USA 1986 November; 83(22):8708-12

Non-patent Document 14: Dellabona P et al., "An invariant V alpha 24-J alpha Q/V beta 11 T cell receptor is expressed in all individuals by clonally expanded CD4−8− T cells", J Exp Med 1994 Sep. 1; 180(3) :1171-6

Non-patent Document 15: Porcelli S et al., "Human T cells expressing an invariant V alpha 24-J alpha Q TCR alpha are CD4− and heterogeneous with respect to TCR beta expression", Hum Immunol 1996 June-July; 48(1-2):63-7

Non-patent Document 16: Makino Y et al., "Predominant expression of invariant V alpha 14+ TCR alpha chain in NK1.1+T cell populations", Int Immunol 1995 July; 7(7):1157-61

Non-patent Document 17: Taniguchi M et al., "Essential requirement of an invariant V alpha 14 T cell antigen receptor expression in the development of natural killer T cells", Proc Natl Acad Sci USA 1996 Oct. 1; 93(20):11025-8

Non-patent Document 18: Makino Y et al., "Development of V alpha 4+ NKT cells in the early stages of embryogenesis", Proc Natl Acad Sci USA 1996 Jun. 25; 93(13):6516-20

Non-patent Document 19: Bendelac A et al. , "CD1 recognition by mouse NK1+ T lymphocytes", Science 1995 May 12; 268(5212):863-5

Non-patent Document 20: Adachi Y et al., "Positive selection of invariant V alpha 14+ T cells by non-major histocompatibility complex-encoded class I-like molecules expressed on bone marrow-derived cells", Proc Natl Acad Sci USA 1995 Feb. 14; 92(4):1200-4

Non-patent Document 21: Kawano T et al., "CD1d-restricted and TCR-mediated activation of V alpha 14 NKT cells by glycosylceramides", Science 1997 Nov. 28; 278(5343):1626-9

Non-patent Document 22: Cui J et al., "Requirement for V alpha 14 NKT cells in IL-12-mediated rejection of tumors", Science 1997 Nov. 28; 278(5343):1623-6

Non-patent Document 23: Morita M, Motoki K, Akimoto K, Natori T, Sakai T, Sawa E, Yamaji K, Koezuka Y, Kobayashi E, Fukushima H., "Structure-activity relationship of alpha-galactosylceramides against B16-bearing mice", J Med Chem 1995 Jun. 9; 38(12):2176-87

Non-patent Document 24: Nakagawa R et al., "Treatment of hepatic metastasis of the colon 26 adenocarcinoma with an alpha-galactosylceramide, KRN7000", Cancer Res 1998 Mar. 15; 58(6):1202-7

Non-patent Document 25: Kawano T et al., "Natural killer-like nonspecific tumor cell lysis mediated by specific ligand-activated V alpha 14 NKT cells", Proc Natl Acad Sci USA 1998 May 12; 95 (10):5690-3

Non-patent Document 26: Kawano T et al., "Antitumor cytotoxicity mediated by ligand-activated human V alpha 24 NKT cells", Cancer Res 1999 Oct. 15; 59(20):5102-5

Non-patent Document 27: Giaccone G et al., "A phase I study of the natural killer T-cell ligand alpha-galactosylceramide (KRN7000) inpatients with solid tumors", Clin Cancer Res 2002 December; 8(12);3702-9

Non-patent Document 28: Motohashi S et al., "A phase I study of in vitro expanded natural killer T cells in patients with advanced and recurrent non-small cell lung cancer", Clin Cancer Res. 2006 Oct. 15; 12(20):6079-86

Non-patent Document 29: Toura I et al., "Cutting edge: inhibition of experimental tumor metastasis by dendritic cells pulsed with alpha-galactosylceramide", J Immunol 1999 Sep. 1; 163(5):2387-91

Non-patent Document 30: Ishikawa A et al., "A phase I study of alpha-galactosylceramide (KRN7000)-pulsed dendritic cells in patients with advanced and recurrent non-small cell lung cancer. Clin Cancer Res 2005 Mar. 1; 11(5):1910-7

Non-patent Document 31: Horiguchi Shigetoshi et al., "In vivo migration of nasal mucosal dendritic cells", Journal of Japan society of Immunology & Allergology in Otolaryngology, 2003 21(2):10-11

Non-patent Document 32: Okamoto Yoshitaka et al., "Cellular immunotherapy and heavy particle therapy introduced for pharyngeal cancer", Chiba University COE report, 2005:116-118

Non-patent Document 33: Fuwa N et al., "A combination therapy of continuous superselective intraarterial carboplatin infusion and radiation therapy for locally advanced head and neck carcinoma", Cancer 2000 Nov. 15; 89(10):2099-105

DISCLOSURE OF THE INVENTION

Problem To Be Solved By the Invention

In view of the above-mentioned circumstances, an object of the present invention is to provide a method of efficiently delivering cells having an anti-tumor activity to tumor tissues in cellular immunotherapy for cancers utilizing cells having anti-tumor activity, antigen presenting cells that activate cells capable of exhibiting anti-tumor activity, and the like, and thereby provoking a stronger anti-tumor reaction. Another object of the present invention is to provide a method of obtaining a more efficient effect on tumor regression in the cellular immunotherapy.

Means For Solving the Problem

As a result of intensive studies to achieve the above-mentioned objects, the inventors found that by infusing NKT cells being activated with α-galactosylceramide into the tumor-feeding artery and transfusing antigen presenting cells treated with α-galactosylceramide through the nasal mucosa, a stronger anti-tumor reaction was provoked as well as stimulation of a systemic immune response, and remarkable tumor regression effect was obtained, and thus achieved the present invention.

That is, the present invention relates to the following:
(1) a method of treating head and neck cancer, comprising administrating an anti-cancer cell composition containing NKT cells activated in vitro with an NKT cell ligand into a tumor-feeding artery of head and neck cancer, and administering an NKT cell stimulating agent containing antigen presenting cells treated with an NKT cell ligand through upper respiratory tract mucous membrane;
(2) a method of treating head and neck cancer, comprising administrating an anti-cancer cell composition containing NKT cells activated in vitro with α-galactosylceramide into a tumor-feeding artery of head and neck cancer, and administering an NKT cell stimulating agent containing antigen presenting cells treated with α-galactosylceramide through nasal mucosa;
(3) a use, in anti-cancer treatment of head and neck, of an anti-cancer cell composition containing NKT cells activated in vitro with an NKT cell ligand wherein the composition is to be administered into a tumor-feeding artery, and an NKT cell stimulating agent containing antigen presenting cells treated with an NKT cell ligand wherein the agent is to be administered through upper respiratory tract mucous membrane;
(4) a use, in treatment of head and neck cancer, of an anti-cancer cell composition containing NKT cells activated in vitro with α-galactosylceramide wherein the composition is to be administered into a tumor-feeding artery, and an NKT cell stimulating agent containing antigen presenting cells treated with α-galactosylceramide wherein the agent is to be administered through nasal mucosa;
(5) a kit, comprising an anti-cancer cell composition containing NKT cells activated in vitro with an NKT cell ligand wherein the composition is to be administered into a tumor-feeding artery, and an NKT cell-stimulating agent containing antigen presenting cells treated with an NKT cell ligand wherein the agent is to be administered through upper respiratory tract mucous membrane;
(6) a kit, comprising a therapeutic agent for head and neck cancer containing NKT cells activated in vitro with α-galactosylceramide wherein the agent is to be administered into a tumor-feeding artery, and an NKT cell-stimulating agent containing antigen presenting cells treated with α-galactosylceramide wherein the agent is to be administered through nasal mucosa;
(7) an anti-cancer cell composition for treatment of head and neck cancer, comprising NKT cells activated in vitro with an NKT cell ligand wherein the composition is to be administered into a tumor-feeding artery; and
(8) An anti-cancer cell composition for treatment of head and neck cancer, comprising NKT cells activated in vitro with α-galactosylceramide wherein the composition is to be administered into a tumor-feeding artery.

Advantage of the Invention

According to the present invention, efficient delivery of cells having an anti-tumor activity to a tumor tissue as well as stimulation of a systemic immune response can be achieved by infusion of the anti-cancer cell composition containing NKT cells activated in vitro with the NKT cell ligand into the tumor-feeding artery, and transfusion of the NKT cell stimulating agent containing antigen presenting cells treated with the NKT cell ligand through the upper respiratory tract mucous membrane. Further, according to the present invention, a strong anti-tumor reaction can be evoked, and hence, an effective tumor regression effect can be provided. For example, because, in most of head and neck cancers, blood supply is provided by the peripheral artery such as the branch of the external carotid artery, a selective intraarterial infusion therapy according to the present invention can be performed to afford an effective tumor regression effect. Further, a medicament according to the present invention and a treatment method using the medicament exhibit milder adverse effects as compared to adverse effects observed in chemotherapy and radiotherapy, and thus reduce burden on patients.

DETAILED DESCRIPTION OF THE INVENTION

The present invention provides: a method of treating head and neck cancer, comprising administrating an anti-cancer cell composition into the tumor-feeding artery, and administering an NKT cell stimulating agent through the upper respiratory tract mucous membrane; a use, in treatment of head and neck cancer, of an anti-cancer cell composition and an NKT cell stimulating agent; a kit comprising the anti-cancer cell composition and the NKT cell stimulating agent; and the anti-cancer cell composition.

"Anti-cancer cell composition" refers to a composition containing cells having an anti-tumor activity as active ingredients. "Anti-tumor activity" refers to a tumor growth suppressing effect, a tumor cytotoxic effect and/or a tumor regression effect. The cells having an anti-tumor activity recognize tumors, and exhibit an anti-tumor activity by producing cytokines such as IFN-γ and exhibiting a potent cytotoxic effect. Examples of the cells having an anti-tumor activity include NKT cells, NK cells, and CTLs, and a more preferable example of the cells includes activated NKT cells. The anti-cancer cell composition may exert a tumor regression effect via an action of the cells having an anti-tumor activity that are active ingredients of the composition, and hence may be used for treatment of cancer. Thus, the term "anti-cancer cell composition" and the term "composition for treatment of cancer" are used exchangeably.

The anti-cancer cell composition according to the present invention contains NKT cells activated in vitro with an NKT cell ligand, and is administered into the tumor-feeding artery. A "tumor-feeding artery" refers to a blood vessel in the vicinity of tumor cells, from which the tumor cells obtain nutrition. The tumor-feeding artery carries blood that contains oxygen and nutrition required for growth of tumors. The anti-cancer cell composition that is administered into the tumor-feeding artery is delivered into a tumor tissue highly efficiently and exerts a strong anti-tumor effect in the tumor tissue, resulting in providing a tumor regression effect. For example, head and neck cancer is mainly controlled by terminal blood vessels, and hence it is possible to perform selective intraarterial infusion. Therefore, the administration of the anti-cancer cell composition into the tumor-feeding artery provides a high therapeutic effect. "Head and neck cancer" means a malignant tumor in a head and neck region, such as nasal/paranasal cancer, pharyngeal cancer, oral cancer, laryngeal cancer, thyroid cancer, or saliva gland cancer. The administration of the anti-cancer cell composition into the tumor-feeding artery may be performed by a conventional method, and may be performed by using a catheter, for example.

"NKT cells" refer to a kind of lymphocytes expressing two antigen receptors, i.e., a T cell receptor (TCR) and an NK cell receptor. NKT cells recognize the later-described "NKT cell ligand" presented on a CD1 (for example, CD1d) molecule by the T cell receptor, on the cells. Unlike ordinary T cells, NKT cells have a very limited repertoire of T cell receptors. For example, the α-chain of the T cell receptor on mouse NKT cells (which may be referred to as Vα14 NKT cells) is encoded by invariant Vα14 and Jα281 gene segments (Non-patent Document 13; Koseki H et al., "Dominant expression of a distinctive V14+ T-cell antigen receptor alpha chain in mice", Proc Natl Acad Sci USA 1991 Sep. 1; 88 (17):7518-22; Lantz O et al., "An invariant T cell receptor alpha chain is used by a unique subset of major histocompatibility class I-specific CD4+ and CD4−8− T cells in mice and humans", J Exp Med 1994 Sep. 1; 180(3):1097-106), and 90% or more of the β-chain is V138, and besides the β-chain may include a limited repertoire of Vβ7 and Vβ2. Further, the T cell receptor on human NKT cells is known to be constructed of a combination of invariant Vα24 having a high degree of homology to mouse Vα14, and Vβ11 closely related to Vβ8.2.

An "NKT cell ligand" refers to a compound that is specifically recognized by a T cell receptor on NKT cells and may specifically activate the NKT cells when being presented on a CD1 molecule. Examples of the "NKT cell ligand" used in the present invention include α-glycosylceramide, isoglobotrihexosylceramide (Zhou D et al., "Lysosomal glycosphingolipid recognition by NKT cells", Science 2004 Dec. 3; 306(5702):1786-9), OCH (Miyamoto K et al., "A synthetid glycolipid prevents autoimmune encephalomyelitis by inducing TH2 bias of natural killer T cells", Nature 2001 Oct. 4; 413(6855):531-4). The α-glycosylceramide is a sphingoglycolipid comprising sugars such as galactose and glucose that are linked to ceramide via α-linkage, and is exemplified by those disclosed in WO 93/05055, WO 94/02168, WO 94/09020, WO 94/24142, WO 98/44928, Science 1997 Nov. 28; 278 (5343):1626-9 (Non-patent Document 21), and the like. In particular, (2S,3S,4R)-1-O-(α-D-galactopyranosyl)-2-hexacosanoylamino -1,3,4-octadecanetriol (in this description, referred to as α-galactosylceramide or α-GalCer) is preferable.

A "NKT cell ligand" as used herein has a meaning including salts thereof. As the salts of the NKT cell ligand, salts with physiologically-acceptable acids (e.g., inorganic acids and organic acids) or bases (e.g., alkali metal salts), and the like, preferably physiologically-acceptable acid addition salts, are used. Examples of such salts include salts with inorganic acids (e.g., hydrochloric acid, phosphoric acid, hydrobromic acid, and sulfuric acid) or salts with organic acids (e.g., acetic acid, formic acid, propionic acid, fumaric acid, maleic acid, succinic acid, tartaric acid, citric acid, malic acid, oxalic acid, benzoic acid, methanesulfonic acid, and benzenesulfonic acid).

Further, the "NKT cell ligand" as used herein has a meaning including solvates (such as hydrates) thereof.

NKT cells derived from any mammals maybe used. Examples of the mammals include humans and mammals other than humans. Examples of the mammals other than humans include: experimental animals including rodents such as mice, rats, hamsters, and guinea pigs, and rabbits; livestock such as pigs, cattle, goats, horses, and sheep; pets such as dogs and cats; and primates such as monkeys, orangutans, and chimpanzees.

NKT cells contained in the anti-cancer cell composition according to the present invention have genotype that is not particularly limited and is generally syngeneic, allogeneic, or xenogeneic relative to subjects to each of which the anti-cancer cell composition according to the present invention is administered, and is preferably syngeneic or allogeneic thereto. In order to avoid a rejection response, the antigen presenting cells are preferably syngeneic relative to subjects to each of which the anti-cancer cell composition according to the present invention is administered, and are more preferably those derived from the subjects (i.e., autologous NKT cells) to each of which the anti-cancer cell composition according to the present invention is administered.

NKT cells may be obtained from tissues (such as lymph nodes, spleen, and peripheral blood) of the above-mentioned mammals by a method known per se. For example, mononuclear cells containing NKT cells may be collected from peripheral blood by specific gravity centrifugation. Further, for example, NKT cells may be isolated by a cell sorter, panning, an antibody magnetic bead method, or the like using an antibody against a cell surface marker expressed specifically on the NKT cells. Examples of the cell surface marker expressed specifically on the NKT cells include Vα24 and Vβ11 in the case of humans.

"NKT cells activated in vitro with an NKT cell ligand" refer to NKT cells activated by in vitro treatment with an NKT cell ligand. NKT cells recognize the NKT cell ligand via a T cell receptor on the cells and are activated.

"Activated NKT cells" refer to NKT cells with enhanced production of cytokines (such as IFN-γ and IL-4) and potent cytotoxic actions via perforin/granzyme B in comparison to those before activation. The activated NKT cells show a strong anti-tumor activity.

In vitro activation of NKT cells with the NKT cell ligand may be performed by a treatment comprising bringing the NKT cell ligand into contact with NKT cells. For example, NKT cells are cultured in a physiological culture medium containing the NKT cell ligand. Further, for example, NKT cells are cultured in a physiological culture medium together with antigen presenting cells treated with the NKT cell ligand. Alternatively, for example, NKT cells are cultured in a physiological culture medium containing the NKT cell ligand, followed by further culturing the cultured NKT cells together with antigen presenting cells treated with the NKT cell ligand. The antigen presenting cells used in the in vitro activation of NKT cells are preferably those that have been treated with the NKT cell ligand and further have been arrested in growth by an irradiation treatment or the like. The antigen presenting cells treated with the NKT cell ligand may be prepared by a method mentioned later. The concentration of the NKT cell ligand in the culture medium may be appropriately determined according to the kind of the NKT cell ligand, and is, for example, 1 to 10,000 ng/ml, preferably 10 to 1000 ng/ml, or more preferably 20 to 200 ng/ml. Examples of the culture medium include basal media (a minimal essential medium (MEM), a Dulbecco's modified minimal essential medium (DMEM), an RPMI 1640 medium, 199 medium, and an AIM-V medium) which may contain suitable additives (such as serum, albumin, buffers, and amino acids). The culture medium may preferably contain interleukin-2 (IL-2) in order to promote the growth of NKT cells. The concentration of IL-2 in the culture medium may be appropriately determined, and is, for example, 10 to 1000 JRU (national standard unit)/ml, preferably 10 to 200 JRU/ml, or more preferably 20 to 200 JRU/ml. The pH of the culture medium is usually about 6 to 8. The culture temperature is usually about 30 to 40° C. The culture period is usually four to fourteen days or preferably six to fourteen days. In addition, it is preferable to wash the activated NKT cells after culturing with a culture medium or a physiological aqueous solution free of any NKT cell ligand before use.

In vitro activation of NKT cells with the NKT cell ligand may also be performed by a treatment comprising bringing the NKT cell ligand into contact with a cell population including plural kinds of cells containing NKT cells. Examples of the cell population including plural kinds of cells containing NKT cells include mononuclear cells prepared from peripheral blood. The mononuclear cells prepared from peripheral blood include T cells, NK cells, and the like in addition to the NKT cells. The treatment comprising bringing the NKT cell ligand into contact with such cell population may be performed in the same method and condition as those of the above-mentioned treatment comprising bringing the NKT cell ligand into contact with NKT cells. The cell population including plural kinds of cells containing the activated NKT cells thus obtained may be used as the activated NKT cells in the present invention.

The anti-cancer cell composition according to the present invention may contain, in addition to the activated NKT cells as active ingredients, cells other than the NKT cells, such as NK cells and T cells. Further, the anti-cancer cell composition may contain the activated NKT cells as a mixture with active ingredients for any other treatment. Further, the anti-cancer cell composition is produced by mixing an effective amount of active ingredients together with one or more kinds of pharmacologically-acceptable carriers, and using any method well known in the art of pharmaceutics. The pharmacologically-acceptable carriers are appropriately selected for use from a variety of substances that are well known. Examples of the pharmacologically-acceptable carriers include buffers and additives such as various salts, serum, albumin, and amino acids.

The anti-cancer cell composition according to the present invention is generally provided in dosage forms such as injections and drops. The anti-cancer cell composition is preferably a suspension in which the activated NKT cells are suspended in a sterile aqueous carrier isotonic to body fluid (such as blood) of a recipient. Examples of the aqueous carrier include physiological saline and phosphate-buffered physiological saline (PBS). Further, the aqueous carrier may be added with a solubilization agent, a buffer, a tonicity agent, a soothing agent, a preservative, a stabilizer, and the like as required.

The concentration of the activated NKT cells contained in the anti-cancer cell composition according to the present invention is in a range of usually about $1 \times 10^5$ to $1 \times 10^{10}$ cells/ml or preferably about $2 \times 10^5$ to $1 \times 10^9$ cells/ml, but is not particularly limited to the range. If the cell concentration is too low, it takes long time for administration and thereby a burden on a patient may increase, while if the cell concentration is too high, cells may be aggregated with each other.

The dosage of the anti-cancer cell composition according to the present invention varies depending on the administration form, age, body weight, kind of diseases, and severity of diseases of a patient, and kind of the NKT cell ligand, and the like, and is administered in general in a dose of usually $1 \times 10^6$ to $1 \times 10^9$ cells or preferably $1 \times 10^7$ to $1 \times 10^9$ cells in terms of the number of activated NKT cells per administration. However, such dosage varies depending on the variety of conditions mentioned above.

Meanwhile, an "NKT cell stimulating agent" refers to a medicament that stimulates NKT cells for activation to enhance production of cytokines (such as IFN-γ and IL-4) from NKT cells and cytotoxic actions of NKT cells via perforin/granzyme B.

The "NKT cell stimulating agent" according to the present invention contains antigen presenting cells treated with the NKT cell ligand and is characterized by being administered through the upper respiratory tract mucous membrane. The administration through the upper respiratory tract mucous membrane make it possible to stimulate NKT cells highly efficiently even by a small number of NKT cell ligand-pulsed antigen presenting cells, and to induce production of interferon-γand stimulate an immune reaction. Further, the administration of the NKT cell ligand-pulsed antigen presenting cells through the upper respiratory tract mucous membrane allows for inducing NKT cells selectively in the cervical lymph node. An "upper respiratory tract mucous membrane" refers to a mucosa present on the surface of the upper respiratory tract from the nasal and the like). Because the nasal mucosa has a large number of cavity to the trachea (nasal cavity, pharynx, tonsil, larynx, trachea, immunocompetent cells and blood vessels, the NKT cell stimulating agent is preferably administered through the nasal mucosa. The nasal mucosa is formed of the superior/middle/inferior turbinate mucosa, the superior/middle/inferior nasal meatus mucosa, the nasal septum mucosa, and the like. The NKT cell stimulating agent is administered more preferably through the inferior turbinate mucosa, or still more preferably through the anterior mucosa of the inferior turbinate mucosa because these mucosae have a large number of immunocompetent cells and are excellent in ease of administration. An "administration through the mucosa" as used herein refers to infusing active ingredients into the lamina propria under the epithelial mucosa.

"Antigen presenting cells" refer to cells that present antigens to lymphocytes to promote activation of the lymphocytes. In general, the antigen presenting cells are dendritic cells or macrophages capable of presenting antigens to T cells and NKT cells. In particular, the dendritic cells have a potent antigen presenting ability, and are capable of presenting antigens via MHC Class I, MHC Class I-like molecules (such as CD1), MHC Class II, and the like expressed on the cell surface, and thereby activating T cells or NKT cells, and hence are preferably used for the present invention. In the present invention, the antigen presenting cells are preferably CD1 (for example, CD1d) expressing cells in order to make an NKT cell ligand to be certainly presented to NKT cells.

Antigen presenting cells derived from any mammals may be used. Examples of the mammals include humans and mammals other than humans. Examples of the mammals other than humans include: experimental animals including rodents such as mice, rats, hamsters, and guinea pigs, and rabbits; livestock such as pigs, cattle, goats, horses, and sheep; pets such as dogs and cats; and primates such as monkeys, orangutans, and chimpanzees.

The genotypes of the antigen presenting cells contained in the NKT cell stimulating agent according to the present invention is not particularly limited, and is generally syngeneic, allogeneic, or xenogeneic to a subject which receives administration of the NKT cell stimulating agent, and is preferably syngeneic or allogeneic thereto. In order to avoid a rejection response, the antigen presenting cells are preferably syngeneic to a subject which receives administration of the NKT cell stimulating agent, and are more preferably those derived from the subject (i.e., autologous dendritic cells) which receives administration of the NKT cell stimulating agent.

Antigen presenting cells may be isolated from tissues (for example, lymph nodes, spleen, peripheral blood and the like) of the above-mentioned mammals by a method known per se. For example, dendritic cells may be isolated by a cell sorter, panning, an antibody magnetic beads method, or the like using an antibody against a cell surface marker expressed specifically on the antigen presenting cells. In the case where the dendritic cells are isolated as the antigen presenting cells, CD11c, MHC Class I, MHC Class I-like molecules (such as CD1), MHC Class II, CD8α, CD85k, CD86, FDL-M1, and DEC-205 may be exemplified as the cell surface marker expressed specifically on the antigen presenting cells.

Further, antigen presenting cells may also be produced by culturing bone marrow cells, mononuclear cells, and the like of the above-mentioned mammals under appropriate conditions for differentiating antigen presenting cells. For example, bone marrow cells that are cultured for about six days in the presence of granulocyte-macrophage colony-stimulating factor (GM-CSF, in some cases, additionally IL-4) differentiate to dendritic cells (bone marrow-derived dendritic cells: BMDCs) (Hemmi H et al., "A Toll-like receptor recognizes bacterial DNA", Nature 2000 Dec. 7;408 (6813):740-5). Further, mononuclear cells (in particular, monocytes, macrophages, and the like) in peripheral blood cultured in the presence of GM-CSF (in some cases, additionally IL-2 and/or IL-4) afford dendritic cells (Motohasi S et al., "Preserved IFN-alpha production of circulating Valpha24 NKT cells in primary lung cancer patients", Int J Cancer 2002 Nov. 10; 102(2):159-65. Erratum in: Int J Cancer 2003 May 10; 104(6):799).

Treatment of antigen presenting cells with an NKT cell ligand results in the antigen presenting cells to be pulsed with the NKT cell ligand. "Antigen presenting cells to be pulsed with an NKT cell ligand" means that an NKT cell ligand is placed on the surface of antigen presenting cells so that the ligand may be presented to NKT cells. To be more specific, it means that an NKT cell ligand is presented on a CD1 molecule expressed on the surface of antigen presenting cells. The treatment of antigen presenting cells with an NKT cell ligand may be achieved by bringing the NKT cell ligand into contact with the antigen presenting cells. For example, the antigen presenting cells are cultured in a physiological culture medium containing the NKT cell ligand. In this case, the concentration of an NKT cell ligand in the culture medium may be appropriately determined depending on the kind of the NKT cell ligand, and is, for example, 1 to 10,000 ng/ml or preferably 10 to 1000 ng/ml. Further, examples of the culture medium include basal media (minimum essential medium (MEM), Dulbecco's modified minimum essential medium (DMEM), RPMI 1640 medium, 199 medium, and AIM-V medium), which may contain appropriate additives (such as serum, albumin, buffers, and amino acids). The pH of the culture medium is usually about 6 to 8. The culture temperature is usually about 30 to 40° C. The culture time is usually four to fourteen days or preferably six to fourteen days. In addition, after cultivation, antigen presenting cells are washed with a culture medium or a physiological aqueous solution which does not contain any NKT cell ligand to remove a free NKT cell ligand, and thereby to isolate NKT cell ligand-pulsed antigen presenting cells.

The NKT cell stimulating agent according to the present invention may contain antigen presenting cells treated with the NKT cell ligand as active ingredients alone or as a mixture with active ingredients for any other treatment. Further, the NKT cell stimulating agent is produced by mixing an effective amount of active ingredients together with one or more kinds of pharmacologically-acceptable carriers, and using any method well known in the art of manufacturing pharmacy.

The NKT cell stimulating agent according to the present invention is generally provided in dosage forms such as injections and drip infusions. The NKT cell stimulating agent is a suspension in which antigen presenting cells treated with the NKT cell ligand are suspended in a sterile aqueous carrier that is isotonic to body fluid (such as blood) of a recipient. Examples of the aqueous carrier include physiological saline and PBS. The aqueous carrier may be further supplemented with a dissolving aid, a buffer, a tonicity agent, a soothing agent, a preservative, a stabilizer, and the like as required.

The concentration of the antigen presenting cells treated with the NKT cell ligand that are contained in the NKT cell stimulating agent according to the present invention is in a range of usually about $1 \times 10^5$ to $1 \times 10^{10}$ cells/ml or preferably about $2 \times 10^5$ to $1 \times 10^9$ cells/ml, but is not particularly limited to the range. If the cell concentration is too low, it takes long time for administration and thereby a burden on a patient may increase, while if the cell concentration is too high, cells maybe aggregated with each other.

The dosage of the NKT cell stimulating agent according to the present invention varies depending on the administration form, age, body weight, kind of diseases, and severity of diseases of a patient, and kind of the NKT cell ligand, and the like, and is generally administered in a dose of usually $1 \times 10^6$ to $1 \times 10^9$ cells or preferably $1 \times 10^7$ to $1 \times 10^9$ cells per administration in terms of the number of antigen presenting cells pulsed with the NKT cell ligand. However, such dosage varies depending on the variety of conditions mentioned above.

The anti-cancer cell composition and the NKT cell stimulating agent according to the present invention are safe because of their mild adverse effects. Therefore, those may be administered to any mammals. Examples of the mammals include the above-mentioned mammals. The mammals are preferably humans.

Administration of the anti-cancer cell composition according to the present invention into the tumor-feeding artery and administration of the NKT cell stimulating agent according to the present invention through the epithelial mucosa are performed in combination. Administration of the anti-cancer cell composition and administration of the NKT cell stimulating agent may be conducted at the same time or on the same day, or on separate days. Preferably, it is suitable to perform single or multiple administration of the NKT cell stimulating agent followed by single or multiple administration of the anti-cancer cell composition. Further, a combination of administration of the anti-cancer cell composition with administration of the NKT cell stimulating agent is regarded as one-course treatment, and such treatment may be repetitively conducted multiple times. Specific examples of the administration include an administration method comprising administrating the NKT cell stimulating agent, administrating the NKT cell stimulating agent again on day 7 after the administration, and administering the anti-cancer cell composition on the following day after the second administration of the NKT cell stimulating agent. The administration frequency, administration interval, and treatment frequency may be appropriately changed depending on the age, body weight, kinds of diseases, severity of diseases, and the like of patients.

Administration of the anti-cancer cell composition according to the present invention into the tumor-feeding artery enables to deliver activated NKT cells highly efficiently into a tumor tissue and thereby to evoke a strong anti-tumor reaction in the tumor tissue resulting in a tumor regression effect. Further, administration of the NKT cell stimulating agent according to the present invention through the epithelial mucosa enables to induce NKT cells selectively in the cervical lymph node. The selectivity is strict, so that the NKT cells are induced selectively in the cervical lymph node on the same side (ipsilateral) to the site of the upper respiratory tract mucous membrane where dendritic cells are administered. For example, when NKT cell ligand-pulsed antigen presenting cells are administered through the right-side nasal mucosa, NKT cells are induced selectively in the right-side cervical lymph node. It has been reported that NKT cells activated with a ligand have such a unique action mechanism as promptly producing a large amount of IFN-γ and IL-4, exerting a potent cytotoxic activity via perforin/granzyme B, subsequently further inducing various immune reactions, and resulting in exerting a strong anti-tumor action (Non-patent Document 23, Non-patent Document 24, and Non-patent Document 25). Thus, by using the administration of the anti-cancer cell composition into the tumor-feeding artery and the administration of the NKT cell stimulating agent through the epithelial mucosa in combination, it is possible to efficiently deliver cells having an anti-tumor activity into a tumor tissue, and stimulate a systemic immune response. Further, the present invention can evoke a strong anti-tumor reaction and provide an effective tumor regression effect. For example, the selective intraarterial infusion therapy according to the present invention can be used for most of head and neck cancers and leads to an effective tumor regression effect, since most of head and neck cancers get blood supply from the peripheral artery such as the branch of the external carotid artery.

As described above, a combined use of the administration of the anti-cancer cell composition according to the present invention into the tumor-feeding artery and the administration of the NKT cell stimulating agent according to the present invention through the epithelial mucosa can induce more potent immune response and anti-tumor reaction, and further provide a more effective tumor regression effect, as compared to the cases where each of the composition and the agent is administered alone. Thus, a combined use of the administration of the anti-cancer cell composition according to the present invention into the tumor-feeding artery and the administration of the NKT cell stimulating agent according to the present invention through the epithelial mucosa can prevent and/or treat cancer diseases such as head and neck cancer.

Hereinafter, the present invention is more specifically described by way of examples. However, the present invention is not in anyway limited to the examples shown below. A study in each of the examples was performed after a target patient had received a sufficient explanation on contents of the study, and had given a written consent of participation in the study.

Example 1

For patients with head and neck cancer, administration of the activated NKT cells into the tumor-feeding artery and administration of the antigen presenting cells treated with α-GalCer through the nasal mucosa were performed. In a five weeks test period, blood was collected from each of the patients on the date of day 0, and the antigen presenting cells treated with α-GalCer were administrated on day 7 and day 13, and the activated NKT cells were administrated on day 14.

(Target Cases)

Patients with head and neck cancer satisfying the following criteria were selected.

Inclusion Criteria;
1. a case with locally recurrent head and neck cancer who completed conventional treatment or who rejected such treatment
2. a case who has obtained definitive histological diagnosis for squamous cell cancer, and is expected to live for 6 months or more
3. a case having measurable lesions
4. age: a case where the age is 20 to 80 at the time of informed consent
5. performance status (an indicator of systemic conditions defined by Eastern Cooperative Oncology Group (ECOG)): 0 to 2
6. a case who meets the following inspection data (measurement results within four weeks before registration)
the number of leukocytes ≥3000/μL, the number of platelets ≥75,000/μL, serum creatine≤1.5 mg/dL, total bilirubin≤1.5 mg/dL, AST (GOT), ALT (GPT)≤2.5×upper reference limit
7. a case from whom in-person written consent has been obtained
8. a case having NKT cells in peripheral blood (10 or more cells/1 ml of peripheral blood)
9. a locally recurrent case having NKT cells capable of growing 100-fold or more in an NKT cell growth test Exclusion Criteria;

1. a case who have undergone surgical therapy, chemotherapy, or radiotherapy within four weeks prior to participation in this clinical study
2. uncontrolled diabetes, interstitial pneumonitis, and pleural effusion, ascites, and pericardial effusion to be treated
3. a case with a history of hepatitis
4. a case with infections to be treated
5. a case positive for an HBs antigen, an HCV antibody, an HIV antibody, or an HTLV-1 antibody
6. a case with simultaneous double cancer
7. a case with serious cardiac diseases, specifically, being classified into Class III or higher in the New York Heart Association (NYHA) heart functional classification)
8. a case with a history of albumin hypersensitivity
9. a case who receives an oral or injectable corticosteroid
10. a female being in pregnancy or possible pregnancy, and a female being under breast-feeding
11. a case with autoimmune diseases
12. a case who contraindicates donor apheresis (unstable angina, atrioventricular block (A-V block) of II degree or higher grade, Wolff-Parkinson-White (WPW) syndrome, complete left bundle branch block, and systolic blood pressure of 90 or less or 170 mmHg or more)
13. a case who is judged by an attending physician to be inappropriate for participation in this clinical study Table 1 shows backgrounds of selected cases.

α-GalCer treatment followed by irradiation were used as antigen presenting cells to re-stimulate the above-mentioned cultured cells. The cells were cultured for a total of fourteen days and used as a cell preparation containing activated NKT cells. After the completion of culturing, the cultured cells were collected, washed 3 times with physiological saline supplemented with 2.5% albumin, and then suspended in 100 ml of physiological saline supplemented with 2.5% albumin. The final inspection (measurements of the number of cells, survival rate, and endotoxin) was performed, and a cell preparation that passed the inspection was used for administration to the same patient.

Preparation of α-GalCer-Pulsed Antigen Presenting cells

A portion of the mononuclear cells that were collected from peripheral blood obtained for preparation of activated NKT cells was cultured for seven to fourteen days in an AIM-V medium (produced by Invitrogen) containing 800 U/ml GM-CSF (produced by GeneTech) and 100 JRU/ml IL-2 (Imunace, produced by Shionogi) and 5% autoserum. On the day before administration, 100 ng/ml α-GalCer (KRN 7000, Kirin Pharma) was added, and the resultant was cultured for one day to afford α-GalCer-pulsed antigen presenting cells (APCs). The cells were washed and then suspended in physiological saline supplemented with 2.5% albumin, and used for administration to the same patient.

Administration Route and Dose of Activated NKT Cells

In a five weeks test period, blood was collected from each of the patients on the date of day 0, and the activated NKT

TABLE 1

| Patient number | Age (years old) | Gender | PS | Diagnosis | Cancer localization | Previous treatment | the number of Vα24 NKT cells (/mL)* |
|---|---|---|---|---|---|---|---|
| 1 | 61 | female | 0 | recurrent hypopharyngeal cancer | pharynx | ST, RT, CT | 329 |
| 2 | 67 | male | 1 | recurrent pharyngeal cancer lung metastasis | cervical esophagus lung | ST, RT, CT | 294 |
| 3 | 40 | male | 1 | external auditory canal cancer invading skull base | skull base | RT, CT | 206 |
| 4 | 74 | male | 1 | recurrent laryngeal cancer | larynx | RT, CT | 70 |
| 5 | 38 | female | 1 | recurrent tongue cancer | tongue | ST, RT, CT | 451 |
| 6 | 58 | male | 1 | recurrent laryngeal cancer lung metastasis | skin flap lung | ST, RT, CT | 21 |
| 7 | 65 | female | 1 | recurrent gingival cancer | upper jaw | ST, RT | 83 |
| 8 | 77 | male | 1 | recurrent cervical esophagus cancer | cervical esophagus | RT, CT | 49 |

Abbreviation: PS, performance status; ST, surgical therapy; RT, radiotherapy; CT, chemotherapy
*the number of peripheral blood Vα24+ Vβ11+ NKT cells at time of start of clinical study (Method)

Preparation of Activated NKT Cells

A patient was subjected to apheresis to obtain peripheral blood mononuclear cells. The mononuclear cells were collected from peripheral blood by centrifugation using a solution of OptiPrep (produced by Nycomed Amersham). A portion of the collected mononuclear cells was cultured, while a remainder of the mononuclear cells was cryopreserved. The separated mononuclear cells were added with 100 JRU/ml IL-2 (Imunace, produced by Shionogi) and 100 ng/ml α-GalCer (KRN 7000, produced by Kirin Pharma), and then cultured in an AIM-V medium supplemented with 5% plasmanate cutter (GIBCO-BRL). After culturing for one week, the cryopreserved mononuclear cells that were subjected to cells were administrated on day 14. On the day before administration, the ratios of the NKT cells in the cultured cells were calculated by flow cytometry. The cells to be administered were adjusted to $5 \times 10^7$ cells in terms of NKT cells and suspended in 100 ml of physiological saline supplemented with 2.5% albumin. The tumor-feeding artery in a patient was identified by angiography to infuse the cell preparation.

The ratio of the activated NKT cells in the cell preparation containing activated NKT cells were calculated by analyzing the expression of Vα24 and Vβ11 on the surface of the cells by flow cytometry. Further, the ratios of $CD3^-CD56^+$ cells (NK cells) and $CD3^+$ cells (including NKT cells and T cells) were calculated by analysis using flow cytometry. Table 2 shows the results.

TABLE 2

| Patient number | Vα24+ Vβ11+ cells (%) | | CD3+ cells (%) | | CD3− CD56+ cells (%) | |
|---|---|---|---|---|---|---|
| | before culture | day 14 | before culture | day 14 | before culture | day 14 |
| 1 | 0.085 | 10 | 41 | 70 | 32 | 28 |
| 2 | 0.020 | 0.59 | 66 | 65 | 23 | 33 |
| 3 | 0.040 | 12 | 49 | 95 | 41 | 3.6 |
| 4 | 0.005 | 7.1 | 67 | 88 | 16 | 5.3 |
| 5 | 0.120 | 44 | 63 | 86 | 6.9 | 11 |
| 6 | 0.003 | 6.8 | 40 | 76 | 46 | 17 |
| 7 | 0.021 | 8.1 | 68 | 69 | 13 | 22 |
| 8 | 0.015 | 1.0 | 19 | 34 | 35 | 56 |

Administration route and dose of α-GalCer-pulsed antigen presenting cells

In a five weeks test period, blood was collected from each of the patients on the date of day 0, and the α-GalCer-pulsed antigen presenting cells were administered through the nasal mucosa on day 7 and day 13. The α-GalCer-pulsed antigen presenting cells were suspended in physiological saline (about 0.2 ml) supplemented with 2.5% albumin and transfused through the basal mucosa of the inferior turbinate of the patient. The dosage of the antigen presenting cells was set to $1 \times 10^8$ cells.

(Evaluation Items)

Evaluation of the Number of NKT Cells

Blood was collected weekly over five weeks before and after administration to evaluate the increase or decrease in peripheral blood NKT cells. The evaluation was conducted by flow cytometry using the following antibody. $CD3^+ V\alpha24^+ V\beta11^+$ cells were defined as the NKT cells. The number of NKT cells in 1 ml of peripheral blood was measured and subjected to a time-course analysis. Further, $CD3^- CD56^+$ cells were defined as the NK cells, and the number of NK cells was measured in time-dependent manner for use as a control.

Mouse anti-human Vα24 monoclonal antibody (C15, produced by Immunotech)

Mouse anti-human Vβ11 monoclonal antibody (C21, produced by Immunotech)

Mouse anti-human CD3 monoclonal antibody (UCTH1, produced by PharMingen)

Mouse anti-human CD56 monoclonal antibody (produced by BectonDickinson)

Evaluation of NKT Cell Function

Blood was collected weekly over five weeks before and after administration, and peripheral blood mononuclear cells were separated and cryopreserved. At six weeks, the cells were thawed and subjected to measurement of the frequency of cells that react with α-GalCer to produce IFN-γ (α-GalCer responsive IFN-γ producing cells) by an ELISPOT assay. The ELISPOT assay was conducted by using a kit (produced by MABTECH) and a nitrocellulose membrane (Millititer, produced by Millipore) in accordance with the producer's instruction. The cells were stimulated by culturing for 18 hours in a serum-free AIM-V medium containing 100 ng/ml α-GalCer. Color development was performed by using a BCIP/NBT system (produced by Bio-Rad). The count of spots was measured objectively by computer imaging analysis.

Tumor Regression Effect

Before treatment and on the final day of the observation period, Neck imaging computed tomography (neck imaging CT) was conducted to measure the maximum tumor diameters. By comparing each other, a tumor regression effect associated with treatment was measured.

(Results)

Response of Peripheral Blood NKT Cells

1) Changes in Number

Figure 1:
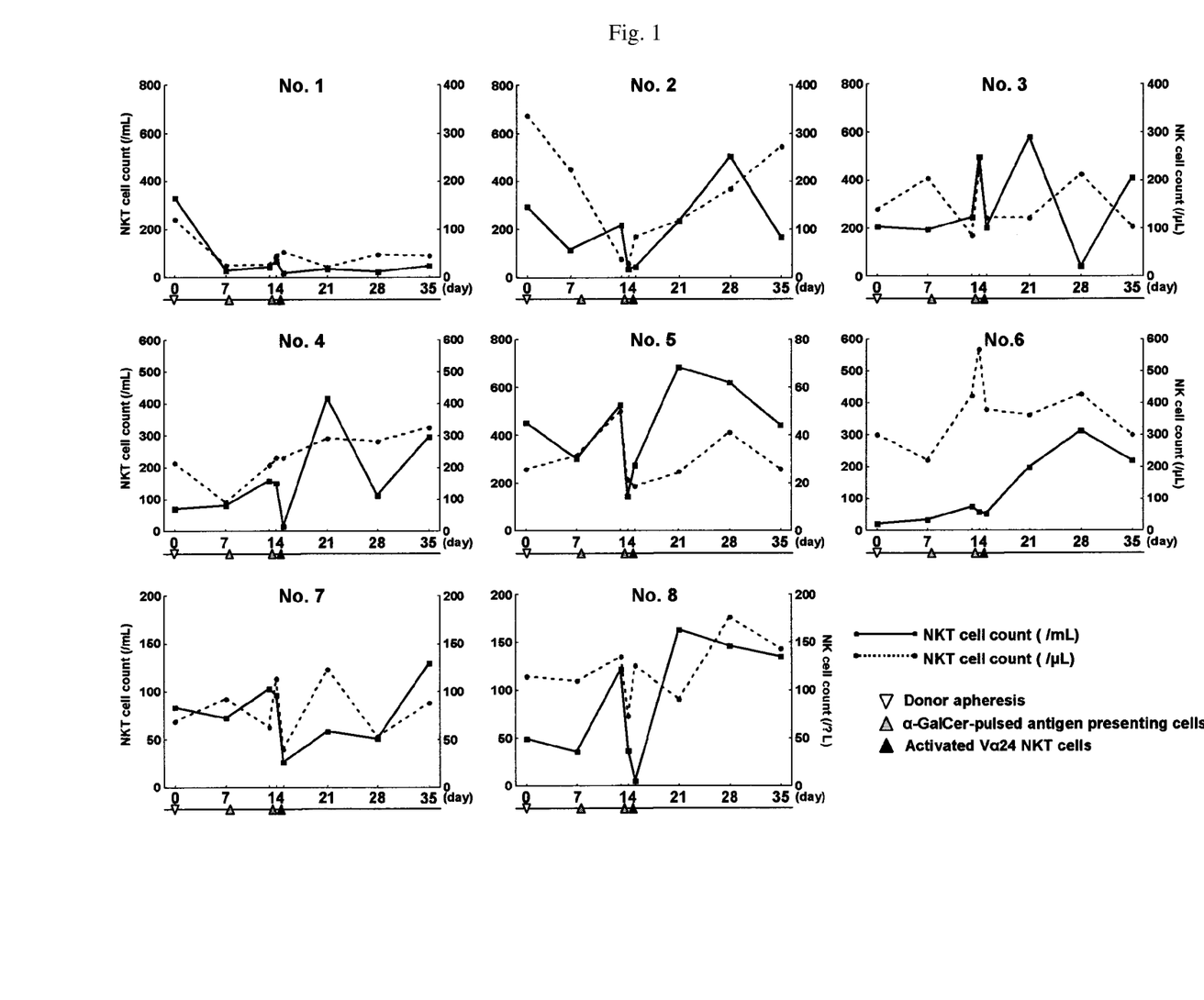
FIG. 1 illustrates changes in the number of NKT cells and the number of NK cells in peripheral blood. The number of NKT cells (full line) and the number of NK cells (dotted line) represent the number of cells in peripheral blood of 1 mL and 1 µL, respectively. Collection of blood components was performed on day 0 (white arrowhead). α-galactosylceramide (α-GalCer)-pulsed antigen presenting cells were transfused through the nasal mucosa on day 7 and day 13 (gray arrowhead), and activated NKT cells were infused into the tumor-feeding artery on day 14 (black arrowhead). In the figures, Numbers 1 to 8 respectively correspond to Cases 1 to 8.

The number of NKT cells and the number of NK cells in 1 mL of peripheral blood are shown in FIG. 1. The peripheral blood NKT cells was increased in four cases, Nos. 2, 3, 5, and 7 (1.7 fold, 2.8 fold, 1.5 fold, and 1.6 fold, respectively), out of eight cases, and remarkably increased in three cases, Nos. 4, 6, and 8 (6 fold, 15 fold, and 3.3 fold, respectively). In all the cases, no clear increase was observed in the number of peripheral blood NK cells.

2) Changes in Function

Figure 2:
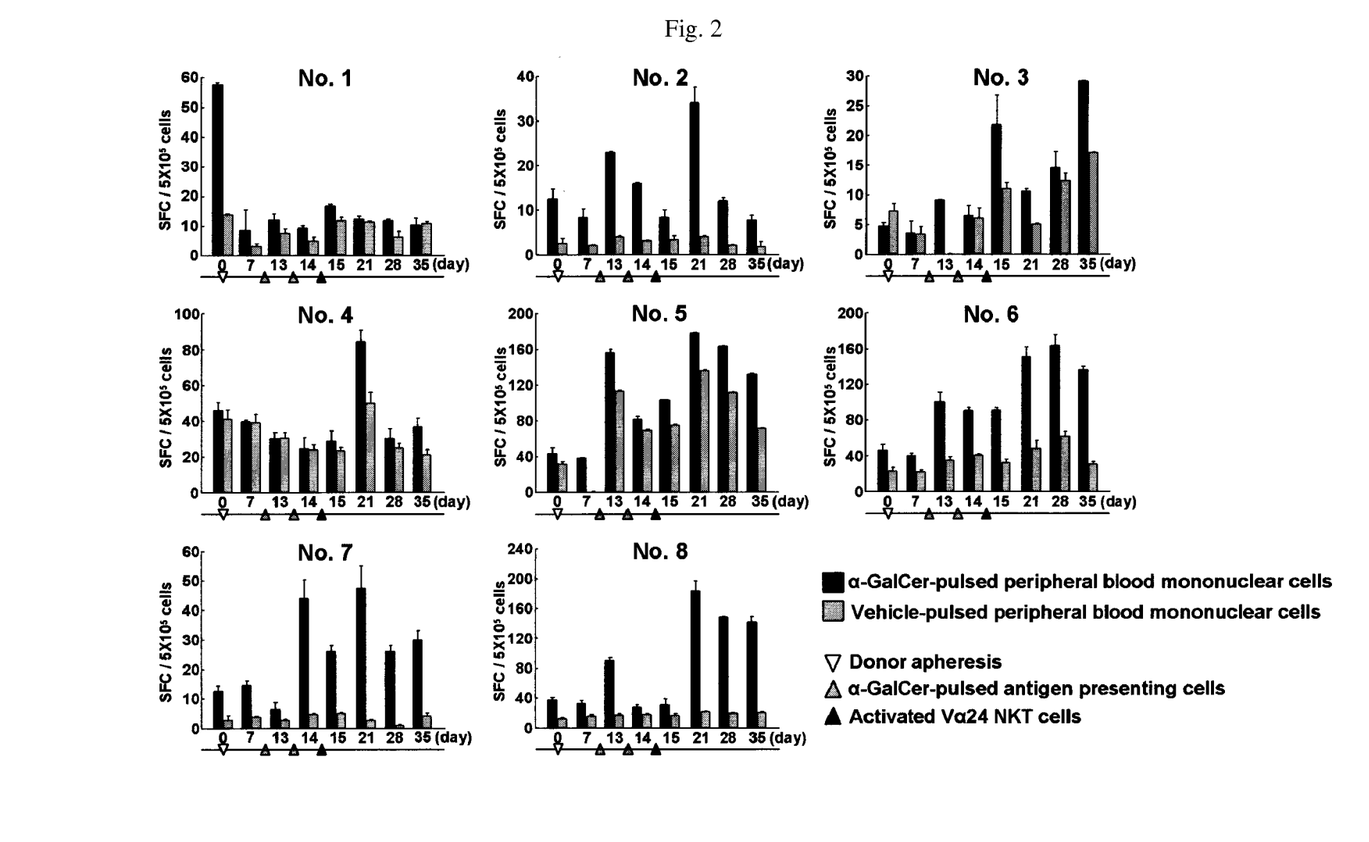
FIG. 2 illustrates changes in the number of α-GalCer responsive IFN-γ producing cells in peripheral blood. The number of α-Galactosylceramide (α-GalCer) responsive IFN-γ producing cells was measured by an ELISPOT assay, and the number of cells was expressed in the number of spot forming cells (SFC) per $5 \times 10^5$ cells. Collection of blood components was performed on day 0 (white arrowhead). α-galactosylceramide (α-GalCer)-pulsed antigen presenting cells were transfused through the nasal mucosa on day 7 and day 13 (gray arrowhead), and activated NKT cells were infused into the tumor-feeding artery on day 14 (black arrowhead). In the figures, Numbers 1 to 8 respectively correspond to Cases 1 to 8.

Changes in the number of α-GalCer responsive IFN-γ producing cells in peripheral blood are shown in FIG. 2. The number of α-GalCer-responsive IFN-γ producing cells was increased in two cases, Nos. 2 and 4 (2.7 fold and 1.8 fold, respectively), out of eight cases, and remarkable increased in five cases, Nos. 3, 5, 6, 7, and 8 (6.3 fold, 4.1 fold, 3.6 fold, 3.7 fold, and 4.9 fold, respectively).

Clinical Effects

Figure 3:
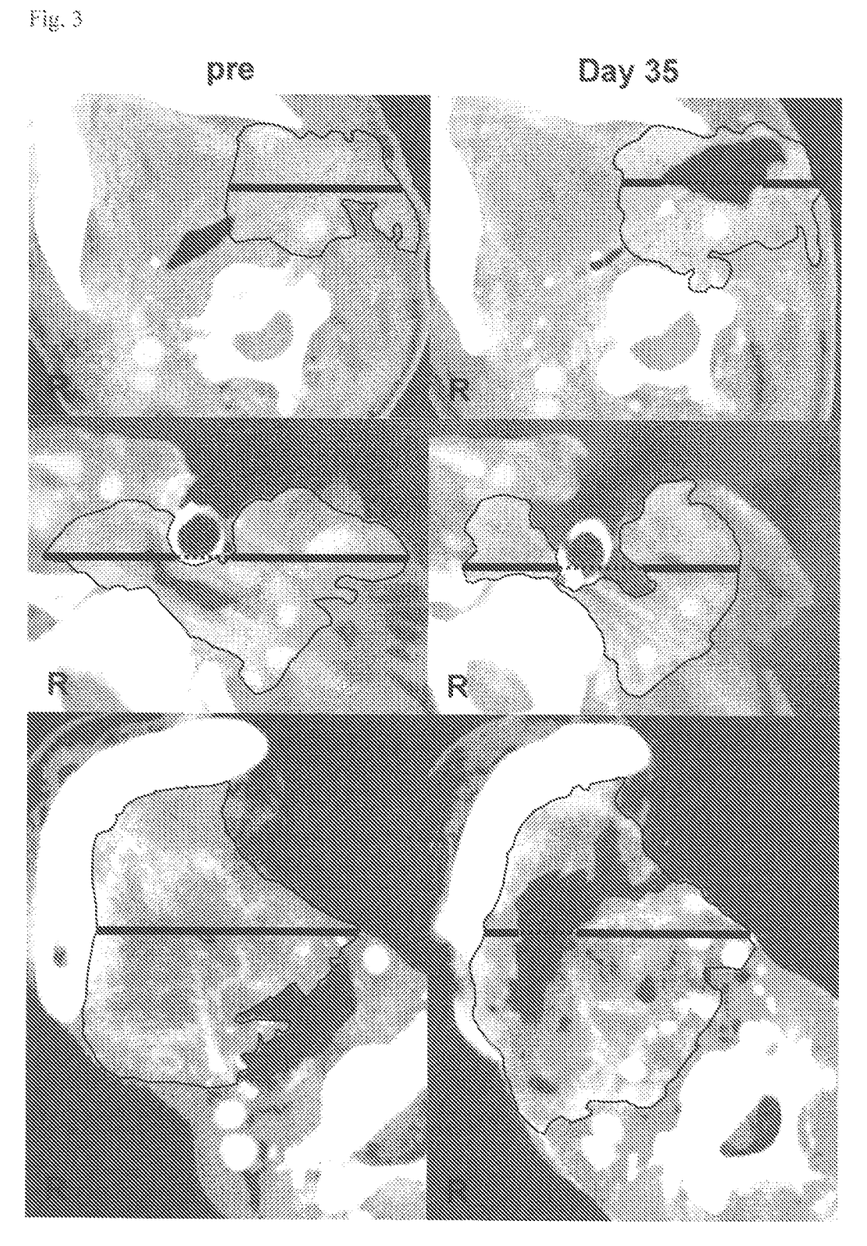
FIG. 3 shows images of neck imaging computed tomography (neck imaging CT) in cases where partial effectiveness was observed. The upper, middle, and lower panels are images of Case 1, Case 2, and Case 5, respectively. The left panels are images taken before treatment (pre) and the right panels are images taken on the final day (Day 35) of an observation period. Regions surrounded by lines represent tumor portions. The maximum tumor diameter is represented by thick lines.

Clinical effects and adverse effects are shown in Table 3. Partial response was observed in three cases (Nos. 1, 2, and 5) out of eight cases, and disease stabilization was observed in four cases. As for the three cases showing partial response, the images of neck imaging CT taken before treatment and on the final day of the observation period are shown in FIG. 3, and the observed values of the maximum tumor diameter measured based on the images and ratios of the maximum tumor diameter on the final day of the observation period to the maximum tumor diameter before treatment are shown in Table 4. Remarkable decrease in maximum tumor diameter was observed in those 3 cases. With respect to the adverse effects, an adverse event corresponding to Grade 3 in National Cancer Institute Common Terminology Criteria for Adverse Events (CTCAE), 3rd Ed. published by the National Cancer Institute was observed in 1 case, but no severe adverse effect was observed in the other cases.

TABLE 3

| Patient number | Adverse event | | | Clinical effect | Tumor size (%) |
|---|---|---|---|---|---|
| | Grade 1 | Grade 2 | Grade 3 | | |
| 1 | Lymphocyte decrease | | Fistula-pharynx | PR | 48 |
| 2 | Lymphocyte decrease | Fever | | PR | 65 |
| 3 | Pain-tumor pain | | | SD | 104 |
| 4 | Fever Pain-headache | | | SD | 109 |
| 5 | Fever | Pain-tumor pain Dehydration | | PR | 65 |
| 6 | Fatigue Vertigo | | | PD | 125 |
| 7 | Pain-tumor pain | Pain-back | | SD | 104 |

TABLE 3-continued

| Patient number | Adverse event Grade 1 | Grade 2 | Grade 3 | Clinical effect | Tumor size (%) |
|---|---|---|---|---|---|
| 8 | Fever Fatigue | | | SD | 110 |

Abbreviation: PR, partial response; SD, stabilized disease; PD, progressive disease

TABLE 4

| | Maximum tumor diameter (mm) | | |
|---|---|---|---|
| Patient | before treatment | day 35 | Tumor size (%) |
| No. 1 | 56.1 | 27.2 | 48.48484848 |
| No. 2 | 66.6 | 43.6 | 65.46546547 |
| No. 5 | 58.3 | 37.7 | 64.66552316 |

Three cases where partial responses were observed are described in more detail.

Case 1: 61-year-old female, recurrent case of hypopharyngeal cancer (T3N2bM0)
Profile of Activated NKT Cells For profiling the activated NKT cells administered, the expression of Vα24 and V1311 on the surface of the cells was analyzed by flow cytometry, with a result that the ratio of Vα24+ Vβ11+ cells was 10% (Table 2).
Response of Peripheral Blood NKT Cells
1) Changes in Number No clear increase was observed in the number of NKT cells and the number of NK cells in 1 mL of peripheral blood (No. 1 in FIG. 1).
2) Changes in Function No clear increase was observed in the number of α-GalCer responsive IFN-γ producing cells in peripheral blood (No. 1 in FIG. 2).
Tumor Regression Effect The tumor necrosis started from the central part, and the tumor maximum diameter decreased to 48% of that before treatment (No. 1 in FIG. 3 and Table 4).

Case 2: 67-year-old male, recurrent case of pharyngeal cancer (T4N2cM0)
Profile of Activated NKT Cells For profiling the activated NKT cells administered, the expression of Vα24 and Vβ11 on the surface of the cells was analyzed by flow cytometry, with a result that the ratio of Vα24+ Vβ11+ cells was 0.59% (Table 2).
Response of Peripheral Blood NKT Cells
1) Changes in Number The number of NKT cells in 1 mL of peripheral blood increased 1.7-fold, while no clear increase was observed in the number of NK cells (No. 2 in FIG. 1).
2) Changes in Function The number of α-GalCer responsive IFN-γ producing cells in peripheral blood increased 2.7-fold (No. 2 in FIG. 2).
Tumor Regression Effect The tumor necrosis started from the central part, and the tumor maximum diameter decreased to 65% of that before treatment (No. 2 in FIG. 3 and Table 4).

Case 5: 38-year-old female, recurrent case of tongue cancer (T2N2bM0)
Profile of Activated NKT Cells For profiling the activated NKT cells administered, the expression of Vα24 and Vβ11 on the surface of the cells was analyzed by flow cytometry, with the result that the ratio of Vα24+ Vβ11+ cells was 44% (Table 2).
Response of Peripheral Blood NKT Cells
1) Changes in Number The number of NKT cells and the number of NK cells in 1 mL of peripheral blood increased 1.5-fold and 1.9-fold, respectively (No. 5 in FIG. 1).
2) Changes in Function The number of α-GalCer responsive IFN-γ producing cells in peripheral blood increased 4.1-fold (No. 5 in FIG. 2).
Tumor Regression Effect The tumor necrosis started from the central part, and the tumor maximum diameter decreased to 65% of that before treatment (No. 5 in FIG. 3 and Table 4).

Hitherto, an intravenous injection therapy of lung cancer with activated NKT cells has been conducted, but no clear tumor regression effect has been observed (Non-patent Document 28).

In contrast, the administration of activated NKT cells into the tumor-feeding artery in this study, which takes advantage of a feature that head and neck cancer is mainly controlled by terminal blood vessels and may be subjected to selective intraarterial injection, resulted in the observation of clear tumor regression effect in three out of eight cases.

The above-mentioned results showed that a tumor regression effect can be obtained by administrating the activated NKT cells into the tumor-feeding artery and administering the NKT cell ligand-pulsed antigen presenting cells through the upper respiratory tract mucous membrane.

The invention claimed is:

1. A method of treating head and neck cancer, comprising
obtaining blood components from a head and neck cancer patient diagnosed with head and neck cancer,
administering an anti-cancer cell composition containing NKT cells obtained from the blood components obtained from the patient and activated in vitro with α-galactosylceramide in an administration number of 1 ×10$^7$ cells to 1 ×10$^9$ cells into a tumor-feeding artery of a head and neck cancer 14 days after obtaining the blood components, and
administering an NKT cell stimulating agent containing physiological carrier and antigen presenting cells obtained from the blood components obtained from the patient and pulsed with α-galactosylceramide that are α-galactosylceramide-pulsed dendritic cells in an administration number of 1 ×10$^7$ cells to 1 ×10$^9$ cells through the basal mucosa of the inferior turbinate of the patient 7 days and 13 days after the obtaining the blood components, and before administering the anti-cancer cell composition.

2. The method of claim 1, wherein the subject has a recurrent head and neck cancer.

3. The method of claim 1, wherein the subject has previously been treated with surgical therapy, radiotherapy, chemotherapy, or any combination thereof.

4. The method of claim 1, wherein the head and neck cancer comprises pharyngeal cancer, auditory canal cancer, laryngeal cancer, tongue cancer, gingival cancer, or esophageal cancer.

5. The method of claim 1, wherein the head and neck cancer comprises a tumor having a diameter and the method of treatment results in a decrease of the tumor diameter.

6. The method of claim 1, wherein the subject is a human patient.

7. The method of claim 1, wherein the administering of the anti-cancer cell composition, the administering of the NKT cell stimulating agent, or both are repeated.

8. The method of claim 1, wherein the carrier is physiological saline.

9. The method of claim 1, wherein the α-galactosylceramide-pulsed dendritic cells are administered in an administration number of $1 \times 10^8$ cells, and the NKT cells activated in vitro with α-galactosylceramide are administered in an administration number of $5 \times 10^7$ cells.

* * * * *